(12) United States Patent
Katdare et al.

(10) Patent No.: US 8,907,084 B2
(45) Date of Patent: Dec. 9, 2014

(54) PROCESS FOR THE PREPARATION OF 2-(2-AMINOETHOXY) ETHANOL (2AEE) AND MORPHOLINE WITH 2AEE: MORPHOLINE >3

(75) Inventors: Sameer Sharad Katdare, Pune (IN); Prasanna Krishna Somalwar, Thane West (IN); Vishwanathan Ramaswamy, Mumbai (IN); Saimani Srinivasan, Pune (IN)

(73) Assignee: Alkyl Amines Chemicals Ltd. (IN)

( * ) Notice: Subject to any disclaimer, the term of this patent is extended or adjusted under 35 U.S.C. 154(b) by 323 days.

(21) Appl. No.: 13/499,964

(22) PCT Filed: Sep. 14, 2010

(86) PCT No.: PCT/IN2010/000622
§ 371 (c)(1),
(2), (4) Date: Apr. 3, 2012

(87) PCT Pub. No.: WO2011/042916
PCT Pub. Date: Apr. 14, 2011

(65) Prior Publication Data
US 2012/0202995 A1  Aug. 9, 2012

(30) Foreign Application Priority Data
Oct. 6, 2009 (IN) .......................... 2306/MUM/2009

(51) Int. Cl.
*C07D 265/30* (2006.01)
*C07C 213/02* (2006.01)

(52) U.S. Cl.
CPC .................................. *C07C 213/02* (2013.01)
USPC .......................................... 544/106; 564/480

(58) Field of Classification Search
CPC .............................. C07C 209/16; C07D 265/30
USPC .......................................... 544/106; 564/480
See application file for complete search history.

(56) References Cited

U.S. PATENT DOCUMENTS

| | | |
|---|---|---|
| 2,412,209 A | 12/1946 | Dickey et al. |
| 3,155,657 A | 11/1964 | Bedoit, Jr. |
| 4,508,896 A | 4/1985 | Templeton |
| 4,532,324 A * | 7/1985 | Renken et al. ............... 544/106 |
| 5,002,922 A | 3/1991 | Irgang et al. |
| 5,288,911 A | 2/1994 | Koppenhoefer et al. |

OTHER PUBLICATIONS

Scifinder, search for product ALDEGA, accessed Jul. 25, 2011.
International Search Report for International Application No. PCT/IN2010/000622, mailed Mar. 23, 2011.

* cited by examiner

*Primary Examiner* — Yong Chu
(74) *Attorney, Agent, or Firm* — Cantor Colburn LLP

(57) ABSTRACT

The invention relates to a process for the production of 2AEE with selectivity towards 2AEE being significantly higher i.e. the ratio of 2AEE:morpholine >3. DEG and Ammonia are reacted in a continuous mode in hydrogen atmosphere in the presence of a catalyst at temperature of 150° C. to 250° C. and pressure of 10 Bar to 20 Bar, the products being separated by distillation. The catalyst used is metal and its oxide or metal oxide on silica or alumina support. The molar ratio of ammonia:DEG is >20 and the molar ratio of hydrogen:DEG is >1, preferably 1-30. The reactants are optionally fed in a downward flow mode. The catalyst charged into the reactor has metal and its oxide or metal oxide equivalent to a metal content of 10% to 70% on the support.

8 Claims, No Drawings

PROCESS FOR THE PREPARATION OF 2-(2-AMINOETHOXY) ETHANOL (2AEE) AND MORPHOLINE WITH 2AEE: MORPHOLINE >3

CROSS REFERENCE TO RELATED APPLICATIONS

This is a U.S. national stage of application No. PCT/IN2010/000622, filed on 14 Sep. 2010. Priority under 35 U.S.C. §119(a) and 35 U.S.C. §365(b) is claimed from Indian Application No. 2306/MUM/2009, filed 6 Oct. 2009, the disclosure of which are also incorporated herein by reference.

FIELD OF THE INVENTION

The invention relates to a process for the preparation of 2-(2-aminoethoxy) ethanol (2AEE) and morpholine with 2AEE:morpholine >3.

BACKGROUND ART

Amination of alcohols such as diethylene glycol (DEG) with aminating agent such as ammonia produces amines such as 2-(2-aminoethoxy) ethanol (2AEE) and morpholine in varying ratios depending on the catalyst used and the reaction conditions. Generally the catalysts used are metals, metal oxides supported on oxides such as silica, alumina, thoria, zirconia and their like. The ammonia:DEG molar ratio is generally in the range up to 50 and the reaction is carried out at temperatures in the range of 100-300° C. and pressures in the range of 10 to 260 Bar. These reactions are carried out in batch, continuous and semi-continuous modes in diverse phases such as liquid, vapour, and liquid-vapour phases.

U.S. Pat. No. 4,532,324 discloses the reductive amination of DEG in the presence of catalyst consisting of cobalt, copper and ceria and/or thoria. The molar ratio of ammonia:DEG is 50, temperatures 150-260° C., pressures of 500-3500 psig. The ratio of the products 2AEE:morpholine is maximum 5 (wt/wt) when the reaction is carried out at 2500 psig and ammonia:DEG molar ratio of 6.

U.S. Pat. No. 4,645,834 discloses the reaction of DEG and ammonia carried out in presence of nickel, cobalt and chromium catalysts on supports such as silica, kieselguhr, alumina or mixtures thereof. The molar ratio of ammonia:DEG is 1-100, preferably 4-16, temperatures 140-280° C., pressures of 125-500 psig. The ratio of the products 2AEE:morpholine is 0.37-2.21.

U.S. Pat. No. 4,709,028 teaches the use of alumina and silica as support and a component selected from Cobalt, Nickel or Copper. The molar ratio of ammonia:DEG is 1-100, preferably 10, temperatures 140-280° C., pressures of 125-500 psig. The ratio of the products 2AEE:morpholine is 0.12 to 0.31.

U.S. Pat. No. 5,288,911 teaches the use of catalyst essentially containing Iron with optional addition of cobalt. The molar ratio of ammonia:DEG is about 10, temperatures 150-300° C., pressures of 50-300 Bar. The ratio of the products 2AEE:morpholine is 14 when operated at 200 Bar and 240° C. under nitrogen and 2AEE:morpholine is 2.4 when operated at 200 Bar and 240° C. under hydrogen using mixed iron and cobalt catalyst.

GB 1530570 teaches use of catalysts selected from Cu, Ni, Cr, Co, Mn, Mo, Pd, Pt, Rh, and their oxides and mixtures thereof. The molar ratio of ammonia:DEG is 1-10, temperatures 190-230° C., pressures of 700-1800 psig, the pressure sufficient to maintain the reactant in the liquid phase. The ratio of the products 2AEE:morpholine is 0.3 to 2.

U.S. Pat. No. 3,155,657 teaches the use of Ru on gamma alumina, charcoal, etc as catalysts. The continuous process uses molar ratio of ammonia:DEG up to 10, temperatures 180-300° C., pressures of 100-300 Bar. The ratio of the products 2AEE:morpholine is 0.3 to 3.1.

U.S. Pat. No. 4,508,896 teaches the use of catalysts selected from copper, nickel, chromium, cobalt, manganese, molybdenum, palladium, platinum, rhodium, oxides of said metals, and mixtures thereof wherein the ammonia:DEG ratio is about 6, the reaction being carried out at a temperature range of 190° C. to 230° C., substantially in the absence of added hydrogen, and at a pressure ranging from 700 psig to about 2200 psig, recovering from the resulting reaction mixture of products in the ratio of 2AEE:morpholine ranging from 0.5 to 1.78. The catalyst optionally uses alumina as support.

U.S. Pat. No. 4,647,663 teaches the use of hydrogenation/dehydrogenation catalysts such as oxides of nickel, copper, cobalt and chromium on supports such as alumina and silica, kieselguhr wherein the metal by weight of the catalyst including support is from 0.01% to 70%, typically between 20 to 40%.

U.S. Pat. No. 2,529,923 teaches the use of catalysts comprising metallic nickel, copper-chromite, copper, nickel chromite, iron, cobalt, titanium, copper, etc on supports such as kieselguhr. The mixture of the catalyst and DEG is saturated with ammonia and autoclaved at temperatures of 160-400° C. to give a mixture of 2AEE and morpholine, in good yields.

U.S. Pat. No. 5,011,926 teaches the use of dual nickel based catalysts with Ni—Cr—Co oxide with Ni on alumina. The molar ratio of ammonia:DEG is 1-10, temperatures 150-300° C., pressures of 200-5000 psig. The ratio of the products 2AEE:morpholine is 0.09 to 0.67.

U.S. Pat. No. 5,166,433 and U.S. Pat. No. 5,002,922 teach use of zirconium oxide as support with mixed metal oxides for reactions of DEG with ammonia. The mixed metal oxides are from 1 to 30% by weight calculated as CuO of oxygen containing compounds of copper and from 1 to 40% by weight each calculated as CoO or NiO respectively, of oxygen containing compounds of Cobalt and of Nickel. These are used for amination of alcohols under hydrogenating conditions. U.S. Pat. No. 5,166,433 claims a process for the amination of alcohols under hydrogenating conditions and U.S. Pat. No. 5,002,922 claims catalyst compositions. The examples cited in these patents use ammonia:DEG ratio of 12.8; temperature of 200° C., pressure of 30 Bar to yield 2AEE:Morpholine of 0.12 to 0.4 and at a pressure of 200 Bar the yield of 2AEE:Morpholine is 0.005 to 0.24.

U.S. Patent Application No 2008/0255351 teaches the use of a catalytically active composition, which prior to treatment with hydrogen, comprises a mixture of oxygen-containing compounds of copper, nickel, cobalt on zirconia, the catalyst being used is small shaped bodies. The ammonia:DEG molar ratio in the examples is 6.5, the temperature is 190-200° C. and pressure of 200 Bar results in 2AEE:morpholine ratio of 0.98, 0.66 and 0.34 when 1.5×2 mm shaped bodies are used at temperatures of 192° C., 195° C., and 198° C. respectively (example no. 1).

In the above patent application no 2008/0255351, the object of the invention as is stated in page 3 paragraph [0038] is to obtain high ADG (aminodiglycol) selectivity when catalyst is used in the form of small shaped bodies.

There is a long felt need in industry to provide cost effective industrial processes for the production of 2AEE wherein The selectivity towards 2AEE is significantly higher, such that the ratio of 2AEE:morpholine >3 is obtained The operating pressures is as low as <20 Bar Thus in accordance with this invention, 2AEE:morpholine ratios of >3 is obtained wherein, DEG and Ammonia is reacted in a continuous mode in hydrogen atmosphere in the presence of a catalyst at temperatures of 150° C. to 250° C. and pressure of 10 Bar to 20 Bar the products being separated by distillation;

the catalyst used is metal and its oxide or metal oxide on silica or alumina or Kieselguhr support the molar ratio of ammonia:DEG being >20;

the molar ratio of hydrogen:DEG being >1; preferably between 1-30 optionally the reactants being fed in a downward flow mode.

The metal and metal oxides are selected from transition metals preferably cobalt or nickel.

The catalyst charged into the reactor has metal and its oxide or metal oxide equivalent to a metal content of 10% to 70% on the support The preferred supports selected from silica or alumina or kieselguhr.

The invention will now be illustrated with non-limiting examples.

EXAMPLE 1

50 gms of catalyst comprising Cobalt Oxide on Alumina (equivalent to 15 wt % Co) was charged in a tubular reactor and reduced at 200° C. under hydrogen flow. DEG (62 gms/hr), ammonia (325 gms/hr) and 53 NL/hr of hydrogen gas was fed in the downflow mode into the reactor at 180° C. and pressure 14 Bar (g) for 6.5 hours to yield weight ratio of 2AEE:Morpholine 4.3

EXAMPLE 2

50 gms of catalyst comprising Cobalt Oxide on Alumina (equivalent to 15 wt % Co) was charged in a tubular reactor and reduced at 200° C. under hydrogen flow. DEG (73 gms/hr), ammonia (382 gms/hr) and 62 NL/hr of hydrogen gas was fed in the downflow mode into the reactor at 180° C. and pressure 14 Bar (g) for 6.5 hours to yield weight ratio of 2AEE:Morpholine 6.2

EXAMPLE 3

50 gms of catalyst comprising Cobalt Oxide on Keiselguhr (equivalent to 40 wt % Co) was charged in a tubular reactor and reduced at 200° C. under hydrogen flow. DEG (62 gms/hr), ammonia (310 gms/hr) and 42 NL/hr of hydrogen gas was fed in the downflow mode into the reactor at 210° C. and pressure 14 Bar (g) for 6.75 hours to yield weight ratio of 2AEE:Morpholine 3.1.

EXAMPLE 4

50 gms of catalyst comprising Cobalt Oxide on Keiselguhr (equivalent to 40 wt % Co) was charged in a tubular reactor and reduced at 200° C. under hydrogen flow. DEG (62.5 gms/hr), ammonia (320 gms/hr) and 43 NL/hr of hydrogen gas was fed in the downflow mode into the reactor at 210° C. and pressure 14 Bar (g) for 7 hours to yield weight ratio of 2AEE:Morpholine 3.8.

EXAMPLE 5

50 gms of catalyst comprising Ni and its oxide on alumina (equivalent to 67 wt % Ni) was charged in a tubular reactor and activated at 200° C. DEG (25.4 gms/hr), ammonia (125 gms/hr) and 14.45 NL/hr of hydrogen gas was fed in the downflow mode into the reactor at 220° C. and pressure 10 Bar (g) for 7 hours to yield weight ratio of 2AEE:Morpholine of 3.7

EXAMPLE 6

50 gms of catalyst comprising Ni and its oxide on alumina (equivalent to 67 wt % Ni) was charged in a tubular reactor and activated at 200° C. DEG (47.51 gms/hr), ammonia (193.7 gms/hr) and 58.17 NL/hr of hydrogen gas was fed in the downflow mode into the reactor at 215° C. and pressure 12 Bar (g) for 8 hours to yield weight ratio of 2AEE:Morpholine of 3.1

EXAMPLE 7

50 gms of catalyst comprising Cobalt Oxide on Keiselguhr (equivalent to 40 wt % Co) was charged in a tubular reactor and reduced at 200° C. under hydrogen flow. DEG 60 (gms/hr), ammonia (317.2 gms/hr) and 49.4 NL/hr of hydrogen gas was fed in the downflow mode into the reactor at 260° C. and pressure 14 Bar (g) for 7 hours to yield weight ratio of 2AEE:Morpholine of 0.9.

EXAMPLE 8

50 gms of catalyst comprising Cobalt Oxide on Keiselguhr (equivalent to 40 wt % Co) was charged in a tubular reactor and reduced at 200° C. under hydrogen flow. DEG 62 (gms/hr), ammonia 145.8 (gms/hr) and 48.6 NL/hr of hydrogen gas was fed in the downflow mode into the reactor at 210° C. and pressure 14 Bar (g) for 7 hours to yield weight ratio of 2AEE:Morpholine of 1.4

The processes in the prior art to yield 2AEE:morpholine ratios >3 are carried out at high pressures of over 200 Bar. In contrast the present invention provides a cost effective and viable industrially scalable process to achieve 2AEE:morpholine ratio >3 at significantly low pressures (<20 Bar) using the catalysts described herein.

We claim:

1. A process to obtain 2-(2-Aminoethoxy)ethanol:morpholine ratios of greater than 3 wherein, Diethylene glycol and Ammonia are reacted in a continuous mode in hydrogen atmosphere in the presence of a catalyst at temperatures less than 250° C. and pressures of less than 20 bar (g) wherein the catalyst is metal and its oxide selected from cobalt or nickel on silica or alumina or Kieselguhr and wherein the molar ratio of ammonia:diethylene glycol is greater than 20.

2. A process as claimed in claim 1 wherein the products are separated by distillation.

3. A process as claimed in claim 1 wherein the temperature is 150° C. to 250° C.

4. A process as claimed in claim 1, wherein the pressure is between 10 bar (g) to 20 bar (g).

5. A process as claim 1 wherein the metal and its oxide is equivalent to metal content of 10% to 70% on the support.

6. A process as claimed in claim 1 wherein the molar ratio of hydrogen:diethylene glycol is greater than 1.

7. A process as claimed in claim 1 wherein the reactants are optimally fed in downward mode.

8. A process as claimed in claim 6, wherein the molar ratio of hydrogen:diethylene glycol is greater than 1 and less than 30.

* * * * *